US00PP22873P2

(12) United States Plant Patent
Mak

(10) Patent No.: US PP22,873 P2
(45) Date of Patent: Jul. 24, 2012

(54) LILY PLANT NAMED 'TINY SPIDER'

(50) Latin Name: *Lilium hybrida*
Varietal Denomination: Tiny Spider

(75) Inventor: Nicolaas Aloysius Maria Mak, 't Zand (NL)

(73) Assignee: Mak 't Zand B.V., 't Zand (NL)

( * ) Notice: Subject to any disclaimer, the term of this patent is extended or adjusted under 35 U.S.C. 154(b) by 45 days.

(21) Appl. No.: 12/927,265

(22) Filed: Nov. 10, 2010

(51) Int. Cl.
*A01H 5/00* (2006.01)

(52) U.S. Cl. ..... Plt./314

(58) Field of Classification Search ..... Plt./314
See application file for complete search history.

*Primary Examiner* — June Hwu
(74) *Attorney, Agent, or Firm* — C. A. Whealy

(57) ABSTRACT

A new and distinct cultivar of Lily plant named 'Tiny Spider', characterized by its upright plant habit; vigorous growth habit; densely-foliated habit; freely flowering habit; upright flower buds; large red purple-colored flowers with greyed purple-colored spots; and good postproduction longevity.

1 Drawing Sheet

Botanical designation: *Lilium hybrida.*
Cultivar denomination: 'TINY SPIDER'.

BACKGROUND OF THE INVENTION

The present Invention relates to a new and distinct cultivar of Lily plant, commercially known as Asiatic Hybrid Lily, botanically known as *Lilium hybrida* and hereinafter referred to by the name 'Tiny Spider'.

The new Asiatic Hybrid Lily plant is a product of a planned breeding program conducted by the Inventor in 't Zand, The Netherlands. The objective of the breeding program was to develop new compact and dense potted Asiatic Hybrid Lily plants with large flowers, attractive flower coloration and good postproduction longevity.

The new Asiatic Hybrid Lily plant originated from a cross-pollination in 2001 of an unnamed proprietary selection of *Lilium hybrida*, not patented, as the female, or seed, parent with an unnamed proprietary selection of *Lilium hybrida*, not patented, as the male, or pollen, parent. The new Asiatic Hybrid Lily plant was discovered and selected by the Inventor as a flowering plant from within the resultant progeny of the cross-pollination in a controlled greenhouse environment in 't Zand, The Netherlands in 2004.

Asexual reproduction of the new Asiatic Hybrid Lily plant by bulb scales in a controlled greenhouse environment in 't Zand, The Netherlands since 2005 has shown that the unique features of this new Asiatic Hybrid Lily plant are stable and reproduced true to type in successive generations.

SUMMARY OF THE INVENTION

Plants of the new Asiatic Hybrid Lily have not been observed under all possible environmental conditions. The phenotype may vary somewhat with variations in environment such as temperature and light intensity without, however, any variance in genotype.

The following traits have been repeatedly observed and are determined to be the unique characteristics of 'Tiny Spider'. These characteristics in combination distinguish 'Tiny Spider' as a new and distinct cultivar of Asiatic Hybrid Lily plant:

1. Upright plant habit.
2. Vigorous growth habit.

3. Densely-foliated habit.
4. Freely flowering habit.
5. Upright flower buds.
6. Large red purple-colored flowers with greyed purple-colored spots.
7. Good postproduction longevity.

Plants of the new Asiatic Hybrid Lily differ primarily from plants of the female parent selection in the following characteristics:

1. Plants of the new Asiatic Hybrid Lily larger flowers than plants of the female parent selection.
2. Plants of the new Asiatic Hybrid Lily and the female parent selection differ in flower color as plants of the female parent selection have light pink-colored flowers.

Plants of the new Asiatic Hybrid Lily differ primarily from plants of the male parent selection in flower color as plants of the male parent selection have pink-colored flowers with fewer spots.

Plants of the new Asiatic Hybrid Lily can be compared to plants of Asiatic Hybrid Lily 'Tiny Sensation', disclosed in U.S. Plant Pat. No. 17,617. In side-by-side comparisons conducted in 't Zand, The Netherlands, plants of the new Asiatic Hybrid Lily differed primarily from plants of 'Tiny Sensation' in the following characteristics:

1. Flower tepals of plants of the new Asiatic Hybrid Lily were more recurved at the apex than flower tepals of plants of 'Tiny Sensation'.
2. Plants of the new Asiatic Hybrid Lily and 'Tiny Sensation' differed in flower color as plants of 'Tiny Sensation' had yellow and dark red bi-colored flowers.

DESCRIPTION OF THE PHOTOGRAPH

The accompanying colored photograph illustrates the overall appearance of the new Asiatic Hybrid Lily plant showing the colors as true as it is reasonably possible to obtain in colored reproductions of this type. Colors in the photograph may differ slightly from the color values cited in the detailed botanical description which accurately describe the colors of the new Asiatic Hybrid Lily plant.

The photograph comprises a side perspective view of a typical flowering plant of 'Tiny Spider' grown in a container.

DETAILED BOTANICAL DESCRIPTION

The aforementioned photograph and following observations and measurements describe plants that were grown during the spring in 15-cm containers in a glass-covered greenhouse in 't Zand, The Netherlands and under cultural conditions and practices typically used in Asiatic Hybrid Lily production. During the production of the plants, day temperatures averaged 16° C., night temperatures averaged 18° C. and light levels were about 6,000 lux. Measurements and numerical values represent averages for typical flowering plants. Plants were 55 days old when the photograph and description were taken. In the following description, color references are made to The Royal Horticultural Society Colour Chart, 2001 Edition, except where general terms of ordinary dictionary significance are used.

Botanical classification: *Lilium hybrida* 'Tiny Spider'.

Parentage:

*Female, or seed, parent*.—Unnamed proprietary selection of *Lilium hybrida*, not patented.

*Male, or pollen, parent*.—Unnamed proprietary selection of *Lilium hybrida*, not patented.

Plant description:

*Plant form/growth habit*.—Upright flowering plant; single erect flowering stem with a terminal cluster of flowers; dense plant habit; vigorous growth habit.

*Plant height, soil level to top of flowers*.—About 50 cm.

*Plant diameter*.—About 22 cm.

*Plant circumference*.—About 70 cm.

*Bulbs*.—Diameter: About 10 cm to 20 cm. Texture: Smooth. Color: Close to 155D.

*Flowering stems*.—Diameter: About 5 mm. Internode length: About 2 cm to 2.5 cm. Strength: Strong. Texture: Smooth, glabrous. Color: Close to 137B.

*Leaves*.—Arrangement: Alternate; simple; sessile. Quantity of leaves per plant: About 57. Length, lower leaves: About 10 cm. Width, lower leaves: About 1.8 cm. Length, upper leaves: About 12 cm. Width, upper leaves: About 2 cm. Shape: Lanceolate. Apex: Acute. Base: Decurrent. Margin: Entire. Texture, upper and lower surfaces: Glabrous, smooth; leathery. Venation pattern: Parallel. Color: Developing and fully expanded leaves, upper surface: Close to 137A; venation, close to 137A. Developing and fully expanded leaves, lower surface: Close to 138A; venation, close to 138A.

Flower description:

*Flower arrangement*.—Single flowers arranged in umbellate inflorescences.

*Flower shape and aspect*.—Flowers are funnel-shaped and when fully opened, tepals flatten and recurve towards the apex; flower buds face upright and flowers face mostly upright.

*Flowering habit*.—Freely flowering habit, large bulbs will produce about six flowers per flowering stem.

*Fragrance*.—Slightly fragrant.

*Natural flowering season*.—Plants flower naturally in June and July in The Netherlands; plants can be flowered year-round in the greenhouse and forced to bloom about 55 days after planting.

*Postproduction longevity*.—Good postproduction longevity, flowers last about 13 days on the plant; tepals not persistent; gynoecium persistent.

*Flower buds*.—Length: About 9 cm. Diameter: About 3 cm. Circumference: About 9 cm. Shape: Lanceolate. Color: Close to 144C, with development close to 59D; sutures, close to 144C.

*Flower size*.—Diameter: About 20 cm. Length (height): About 4 cm.

*Perianth*.—Quantity/arrangement: Six tepals per flower; tepals imbricate. Tepal length, inner tepals: About 9.5 cm. Tepal width, inner tepals: About 5.5 cm. Tepal length, outer tepals: About 10 cm. Tepal width, outer tepals: About 3.5 cm. Tepal shape: Lanceolate. Tepal apex: Acute. Tepal margin: Entire. Tepal texture, upper and lower surfaces: Smooth, glabrous. Tepal color: When opening, upper and lower surfaces: Close to 59D; spots, close to 187A. Fully opened, upper and lower surfaces: Close to 59D and 144C.

*Pedicels*.—Angle: About 45° to 70° from stem axis. Strength: Strong. Length: About 6.5 cm. Diameter: About 5 mm. Texture: Smooth, glabrous. Color: Close to 137B.

*Reproductive organs*.—Stamens: Quantity per flower: About six. Filament length: About 6 cm. Filament color: Close to 59C. Anther length: About 1 cm. Anther color: Close to 31C. Pollen amount: Moderate. Pollen color: Close to 169A. Pistils: Quantity per flower: One. Style length: About 4.5 cm. Style color: Close to 171A.

*Fruits*.—Length: About 1.8 cm. Diameter: About 5 mm. Color: Close to 145A.

*Seed produced*.—No viable seeds observed.

Disease/pest resistance: Resistance to pathogens and pests common to Asiatic Lilies has not been observed.

Garden performance: Plants of the new Asiatic Hybrid Lily have exhibited good tolerance to rain and wind and have been observed to tolerate temperatures from about −2° C. to about 40° C.

It is claimed:

1. A new and distinct Lily plant named 'Tiny Spider' as illustrated and described.

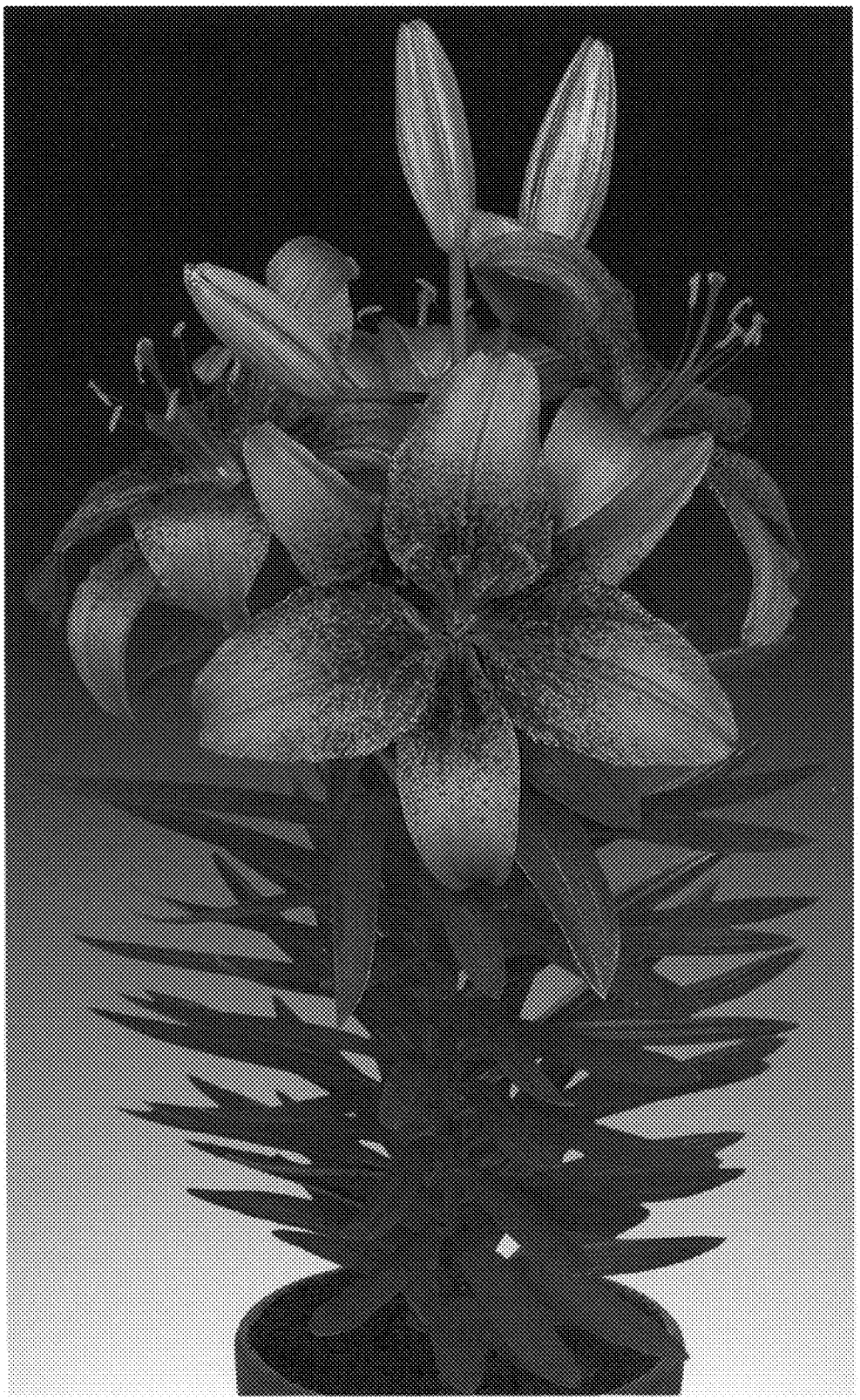

* * * * *